US012390628B2

(12) United States Patent
Duell (10) Patent No.: US 12,390,628 B2
(45) Date of Patent: Aug. 19, 2025

(54) SCALP ROLLER AND METHOD FOR TATTOOING

(71) Applicant: Garrett Paul Duell, Phoenix, AZ (US)

(72) Inventor: Garrett Paul Duell, Phoenix, AZ (US)

( * ) Notice: Subject to any disclaimer, the term of this patent is extended or adjusted under 35 U.S.C. 154(b) by 437 days.

(21) Appl. No.: 17/833,969

(22) Filed: Jun. 7, 2022

(65) Prior Publication Data

US 2023/0390542 A1    Dec. 7, 2023

(51) Int. Cl.
*A61M 37/00* (2006.01)
*A61K 8/02* (2006.01)

(52) U.S. Cl.
CPC ....... *A61M 37/0084* (2013.01); *A61K 8/0204* (2013.01); *A61M 2210/06* (2013.01)

(58) Field of Classification Search
CPC .......... A61M 37/0084; A61M 2210/06; A61M 37/0076; A61M 2210/04; A61M 2037/0023; A61M 37/0015; A61M 2037/0061; A61M 37/00; A61M 5/3287; A61M 2005/1585; A61M 2005/3289; A61M 2037/003; A61M 2037/0046; A61M 2037/0053; A61M 2205/8206; A61M 5/20; A61M 5/3134; A61M 5/3137; A61M 5/31511; A61M 5/31575; A61M 5/31583; A61M 5/3293; A61M 5/3295; A61M 5/3297; A61M 5/3298; A61M 5/425; A61M 5/46; A61K 8/0204; A61K 2800/43; A61K 2800/874; A61K 8/04; A45D 34/041; A61Q 1/025; A61B 17/205; A61B 17/32093; A61B 17/322; A61B 2017/00747; A61B 2017/00765; A61B 2090/395; A61B 90/39; B05C 17/0355; B05C 17/00; B05C 17/0235; B05C 17/02; B05C 17/025; B05C 17/0308; B05C 17/0215
See application file for complete search history.

(56) References Cited

U.S. PATENT DOCUMENTS

| | | | | |
|---|---|---|---|---|
| 2,932,043 | A * | 4/1960 | Bischoff | B05C 17/02 401/36 |
| 3,436,161 | A * | 4/1969 | Charos | B05C 17/025 101/367 |
| 4,409,896 | A * | 10/1983 | Hamisch, Jr. | B41F 31/26 101/367 |
| 6,142,921 | A * | 11/2000 | Wakat | B05C 17/0207 15/230.11 |
| 6,284,075 | B1 * | 9/2001 | Kaplan | B44C 1/04 156/578 |
| 10,625,296 | B1 * | 4/2020 | Velez | B05C 17/025 |

(Continued)

FOREIGN PATENT DOCUMENTS

GB        2296891 A  *  7/1996 ......... B05C 17/0207

*Primary Examiner* — Ashley L Fishback
*Assistant Examiner* — Chima U Igboko
(74) *Attorney, Agent, or Firm* — Bruce A. Lev (57) ABSTRACT

A scalp roller and method for tattooing a person's scalp that includes using a roller having a hollow cylindrical body adapted to retain ink therein, and an outer sleeve having a pattern formed thereon that is adapted to be placed around the outer surface of the cylindrical body and soak up ink therefrom, such that ink can be rolled upon the scalp of a person to form a pattern on the person's scalp, and wherein the person can change the look, size, and/or shape of the pattern before a tattoo is applied to the person's scalp.

10 Claims, 6 Drawing Sheets

(56) References Cited

U.S. PATENT DOCUMENTS

| | | | |
|---|---|---|---|
| 2013/0056020 A1* | 3/2013 | Wilson | A45D 34/041 |
| | | | 132/320 |
| 2014/0079686 A1* | 3/2014 | Barman | A61B 17/00491 |
| | | | 424/94.67 |
| 2014/0234006 A1* | 8/2014 | Nicolulis | B05C 17/0232 |
| | | | 401/208 |
| 2017/0172280 A1* | 6/2017 | Malafarina | A45D 29/00 |
| 2018/0214907 A1* | 8/2018 | Roe | B05C 17/0217 |
| 2022/0313537 A1* | 10/2022 | Shadduck | A61M 35/003 |

* cited by examiner

SCALP ROLLER AND METHOD FOR TATTOOING

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. 37 CFR 1.71(d).

BACKGROUND OF THE INVENTION

1. Field of the Invention

This invention relates generally to cosmetic tattooing of the scalp, and more specifically to scalp rollers and methods for replicating the look of having a scalp tattoo.

2. Description of the Related Art

Prior art methods for tattooing a person's scalp include drawing lines on a person's scalp and then using a tattooing machine to tattoo the person's scalp within the lines drawn. The problem exists wherein a person does not like the look, size, and/or shape of the tattoo, but cannot do anything about it after the tattoo is applied.

Furthermore, there are a number of problems facing practitioners of scalp micropigmentation industry when consulting with their clients regarding their desired cosmetic appearance. Firstly, where the new hairline should be. Potential clients, usually bald (without hair on top of their head), are new to the concept of a hair tattoo/scalp micropigmentation (SMP) and therefore, do not know what hairline would look best on them. The current method scalp artists/practitioners are using to convey to the client the best look for them is to draw out where their hairline should be by making little marks above their forehead indicating where their hairline should start. This puts the job of picturing what it is going to look like on the customer's own imagination. This is bad because the customer is not experienced with SMP enough to know what this will look like based on just some border marks on their head and therefore does not feel 100% comfortable with their hairline decision. Secondly, false expectations. The potential client who is bald may have a different expectation of how the actual SMP points on their head will look. The client may be expecting larger points on their head to represent hair follicles. The client may be expecting finer and smaller points to be present on their head to represent hair follicles. The client may also be expecting the points to not look big or fine, but instead to have an indistinguishable faded/blurred look to them so that no individual point can be seen; just a shading effect. Clients having one of these expectations and then having the results not line up correctly in their mind is a problem for both the provider and the client. Thirdly, painful and time consuming attempts to give the clients a preview. At present, when a provider attempts to show the client what it will look like with SMP done to their head, they sometimes will use a type of ink that will disappear in a few weeks or a few months. This method requires hours and hours to do and will involve all the same needling involved in doing a real SMP head tattoo, So it is a lot of work for the provider and a lot of pain for the customer. All of this just to get an idea of what it will look like. And then, if they agree to move forward, they will have to do it all over again. Presently, there is no solution for a potential client/recipient of SMP to feel 100% confident that what they sign up for is what they will get when they commit to their serious and expensive SMP job.

Accordingly, the present invention overcomes the disadvantages associated with the prior art, by providing a scalp roller that is adapted and used to roll a removable ink pattern on top of the scalp of a person to thereby allow a person to see what the tattoo will look like, and make adjustments thereto before the actual tattoo is applied.

BRIEF SUMMARY OF THE INVENTION

In view of the foregoing disadvantages inherent in the known types of rollers and tattooing machines or the like in the prior art, the present invention provides a new and useful scalp roller and method for tattooing a person's scalp. As such, the general purpose of the present invention, which will be described subsequently in greater detail, is to provide a scalp roller and method for tattooing a person's scalp that includes using a roller having a hollow cylindrical body adapted to retain ink therein, and an outer sleeve having a pattern formed thereon that is adapted to be placed around the outer surface of the cylindrical body and soak up ink therefrom, such that ink can be rolled upon the scalp of a person to form a pattern on the person's scalp, and wherein the person can change the look, size, and/or shape of the pattern before a tattoo is applied to the person's scalp, with all the advantages of the prior art and none of the disadvantages.

There has thus been outlined, rather broadly, the more important features of the invention in order that the detailed description thereof that follows may be better understood and in order that the present contribution to the art may be better appreciated.

Numerous objects, features and advantages of the present invention will be readily apparent to those of ordinary skill in the art upon a reading of the following detailed description of presently preferred, but nonetheless illustrative, embodiments of the present invention when taken in conjunction with the accompanying drawings. The invention is capable of other embodiments and of being practiced and carried out in various ways. Also, it is to be understood that the phraseology and terminology employed herein are for the purpose of descriptions and should not be regarded as limiting.

BRIEF DESCRIPTION OF THE DRAWINGS

The figures which accompany the written portion of this specification illustrate embodiments according to the teachings of the present invention.

The various embodiments of the present invention will hereinafter be described in conjunction with the appended drawings.

DETAILED DESCRIPTION

The embodiments of the present disclosure described below are not intended to be exhaustive or to limit the disclosure to the precise forms disclosed in the following detailed description. Rather, the embodiments are chosen and described so that others skilled in the art may appreciate and understand the principles and practices of the present disclosure.

The following embodiments and the accompanying drawings, which are incorporated into and form part of this disclosure, illustrate embodiments of the invention and together with the description, serve to explain the principles of the invention. To the accomplishment of the foregoing and related ends, certain illustrative aspects of the invention are described herein in connection with the following description and the annexed drawings. These aspects are indicative, however, of but a few of the various ways in which the principles of the invention can be employed and the subject invention is intended to include all such aspects and their equivalents. Other advantages and novel features of the invention will become apparent from the following detailed description of the invention when considered in conjunction with the drawings.

Both providers and recipient of scalp micropigmentation (SMP) know how hard it is to imagine what their new look will be once you they receive SMP. The solutions out there are simply not enough. People want to see their new look in person. They want to feel it with their hands and look at it from different angles. The only way to do this is to quickly, within minutes, put the points on the surface of their skin that look very similar to the real SMP process. The instant invention is essentially pre-manufactured dots on a roller that are then rolled onto a bald head by doing four or five 10 inch-long strokes across the top of their head. Once that is complete, they will have the SMP points replicated on their head (not needled into the skin like real SMP). Then, the practitioner modifies the hairline slightly by wiping excess points away to give it the desired look, and then they can see their new hairline in the mirror. After the points on their head dry and are locked in using other elements of this invention, the client can then actually touch their head and get the full experience of having real SMP done to their head.

Essential Aspects include, allowing the provider to manipulate the hairline as they see fit while the "rolled on" points are still wet and can be wiped away. This invention, with its super fine points, will allow the client to see what the individual points of their final SMP job will look like. This invention allows for a quick application via a dot roller mechanism. This invention allows for the results to be locked in for a period of time so the client can touch their head and spend a day with the results without ruining it. Preferably, this invention will have points or dots on the rolling device that will replicate the look of individual shaved hair follicles. Preferably, the roller never needs to be dipped in ink to achieve these continuous dots on the skin. Preferably, the invention is accompanied with other tools that allow a practitioner to modify the dots left on the client's scalp by removing some or adding some and then being able to lock in the results so the client can then touch their own head.

Referring now to FIGS. 1-6, the present invention discloses a scalp roller 100 for tattooing comprising a handle 110 including a grip portion 112 adapted to be manipulated by a user's hand, and at least one roller attachment member 114 connected to the grip portion and is adapted to rotatably and releasably hold a roller member thereto; and a roller member 120 including a hollow cylindrical body 122 including a plurality of spaced apertures 123, wherein the hollow cylindrical body defines an interior volume adapted to hold liquids 125 therein, colored ink in the preferred embodiment, and is adapted to allow the liquids to pass through the plurality of spaced apertures, and an outer sleeve 124 adapted to be placed around and be removably attached to an outer surface of the hollow cylindrical body 122, wherein the outer sleeve 124 is adapted to soak up the liquids passing through the plurality of spaced apertures 123 and become saturated with the liquids 125, and wherein the outer sleeve is formed to include a pattern 127 formed on an outer surface thereof, such that when the outer sleeve is saturated with the liquids, the liquids can be rolled upon a scalp 500 of a person via the roller member and form the pattern 129 on the person's scalp. The roller member 120 is further adapted to be filled with colored ink and releasably attached to the at least one roller attachment member 114, and wherein the scalp roller 100 is adapted to be used to place the pattern upon the person's scalp.

Figure 1:
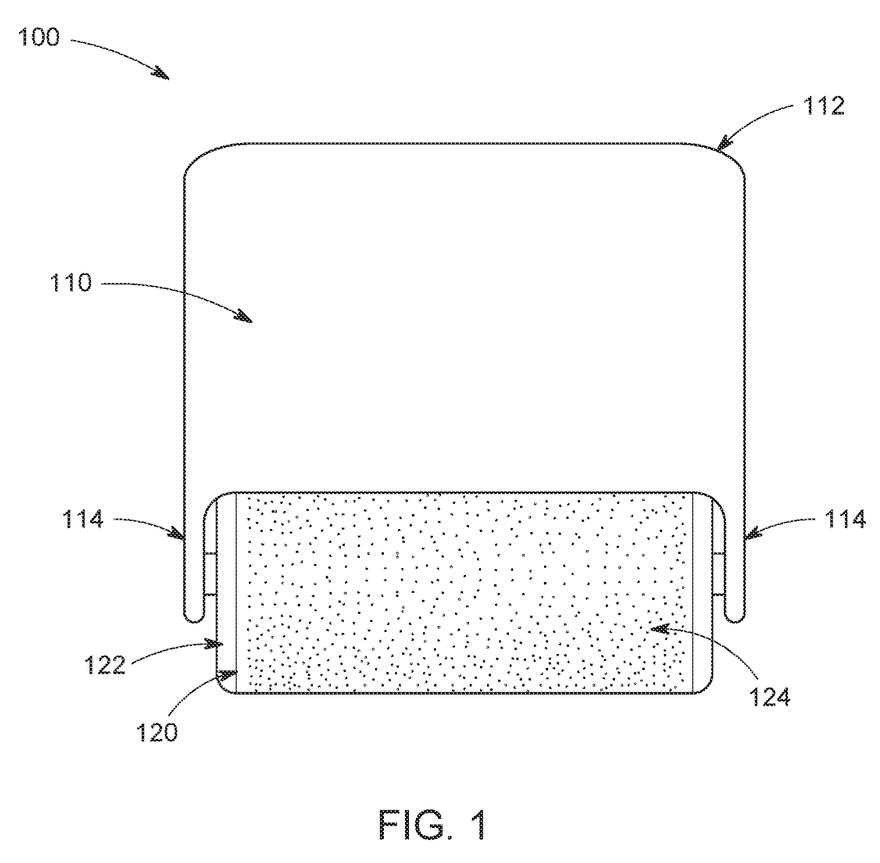
FIG. 1 shows a front view of the scalp roller according to the preferred embodiment of the present invention.
Figure 2:
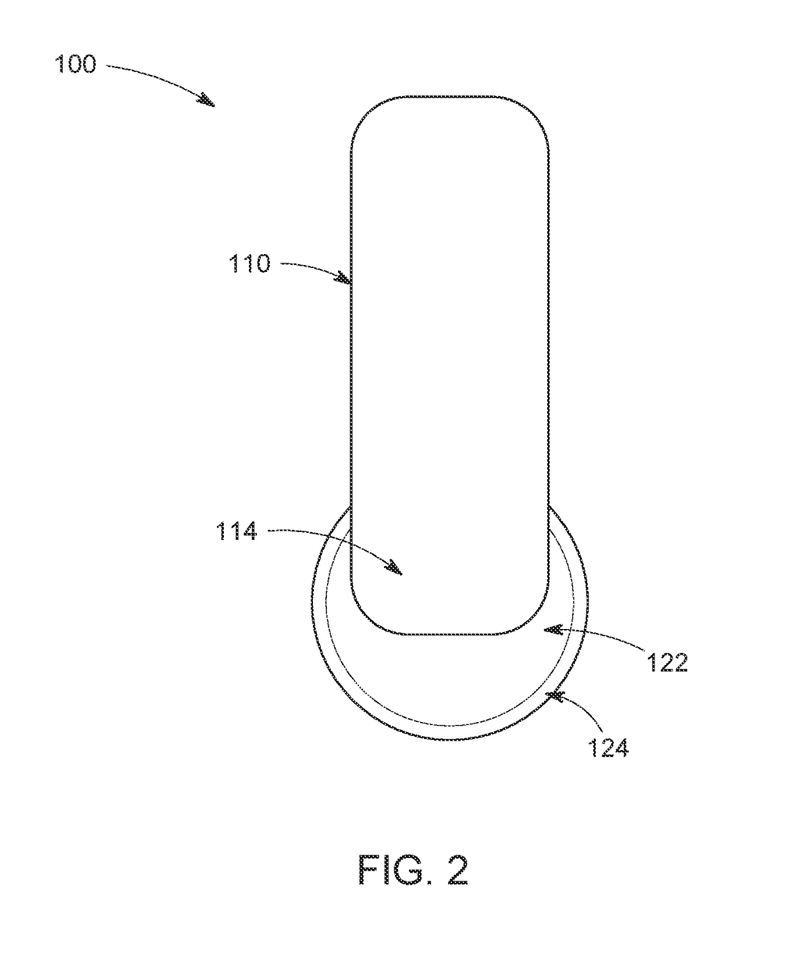
FIG. 2 shows a side view of the scalp roller according to the preferred embodiment of the present invention of FIG. 1.
Figure 3:
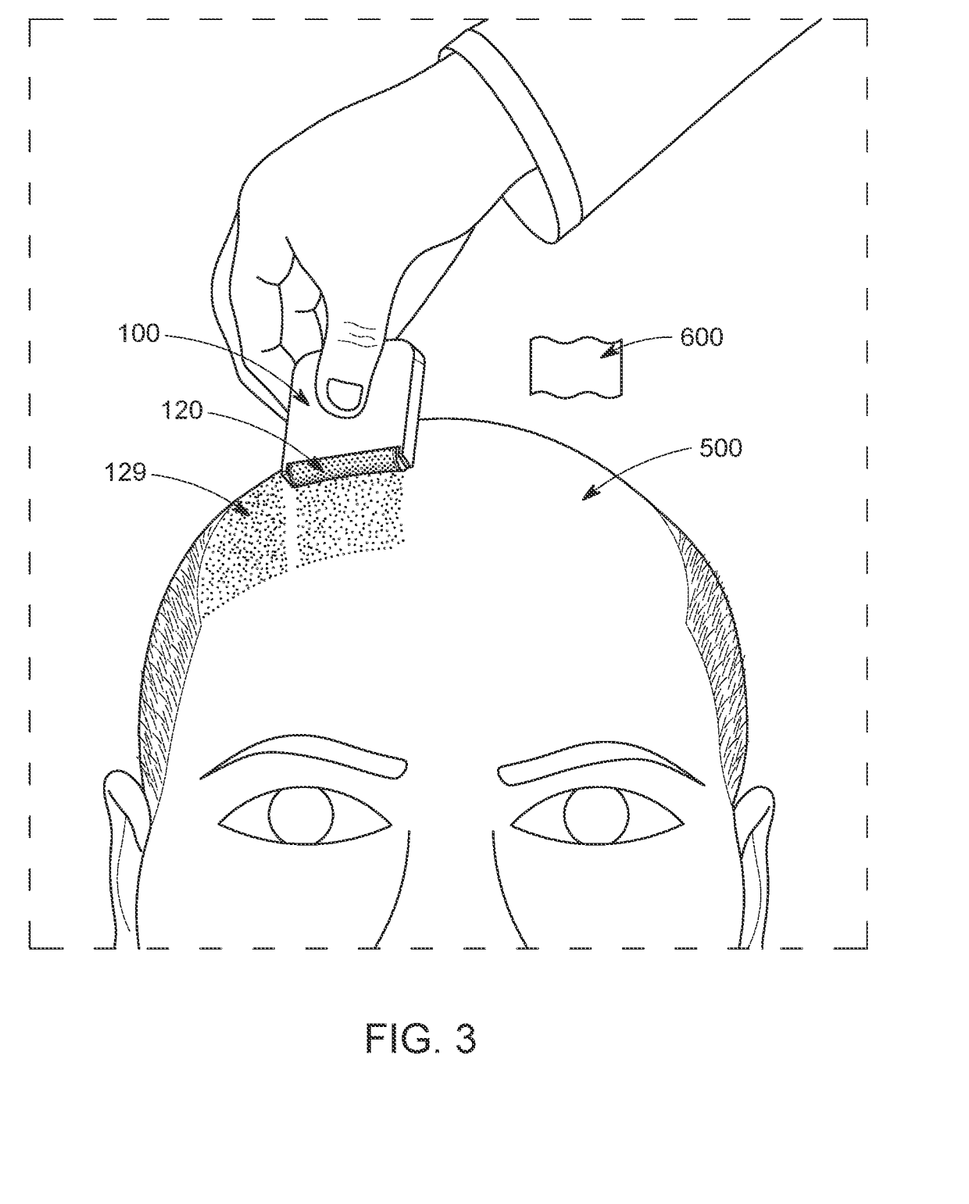
FIG. 3 shows the scalp roller in-use according to the preferred embodiment of the present invention of FIG. 1.

In the preferred embodiment, the scalp roller 100 is formed having two spaced roller attachment members 114 adapted to rotatably hold the roller member therebetween. Furthermore, as shown in FIG. 3, the hollow cylindrical body 122 and the outer sleeve 124 can be formed as being flexible, such that the hollow cylindrical body and said outer sleeve can be adapted to flex and conform to the curvature of said person's scalp 500. The flexibility of the roller member and the outer sleeve can be achieved via the material they are formed by being flexible, such as flexible plastics. In other embodiments, the hollow cylindrical body can be formed as having multiple sections that are pivotally connected to one another, and wherein the outer sleeve is formed from a flexible material that conforms to the shape of the hollow cylindrical body.

In the preferred embodiment, as shown in FIG. 3, the scalp roller pattern 129 is formed to create a pattern on the person's scalp similar to spaced hair follicles. As such, the person can see what the tattoo will look like upon their scalp. In most cases, the person will choose a pattern that would reflect the thickness of their hair when they were younger and/or when they had hair.

Figure 4:
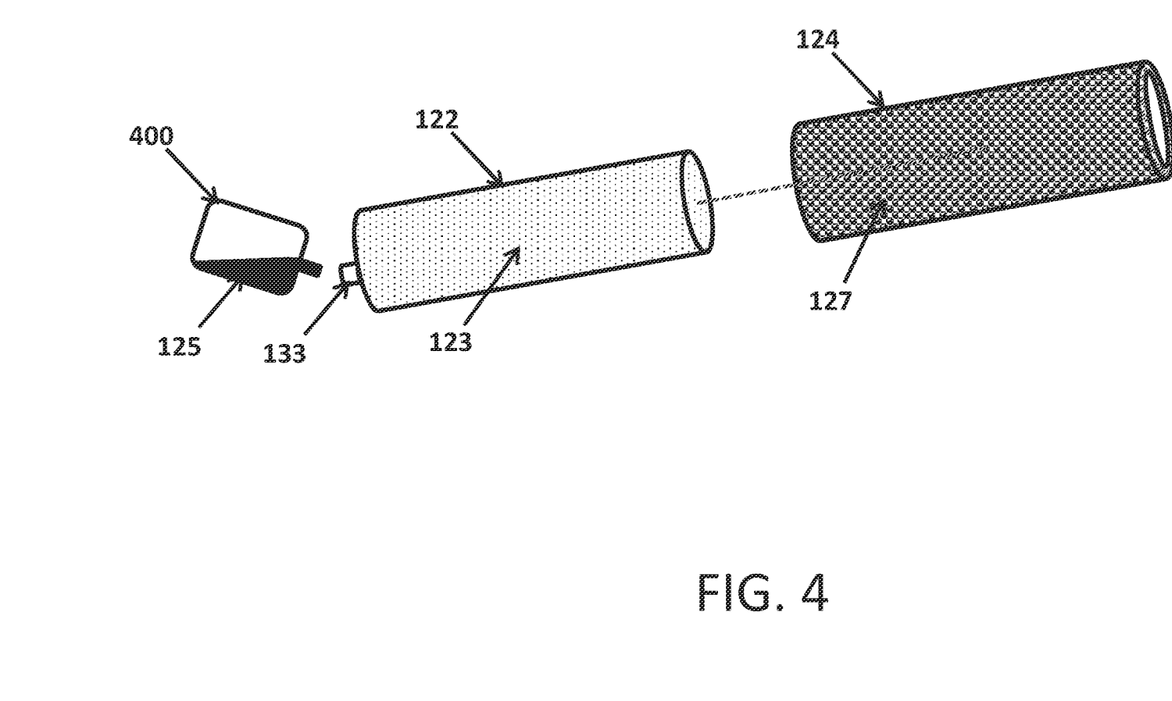
FIG. 4 shows an exploded view of scalp roller being filled with ink according to the preferred embodiment of the present invention of FIG. 1.

The ink used within the hollow cylindrical body will be colored and usually between shades of brown and black and is adapted to be rolled upon the person's scalp via the roller member 120 in the pattern of the chosen outer sleeve. Furthermore, the preferred way of refilling the roller member with liquids is via a nipple 133 located on the hollow cylindrical body 122 adapted to allow liquids, via liquid injector bottle 400, to be injected into the interior volume of the hollow cylindrical body and not spill outwardly therefrom.

Figure 5:
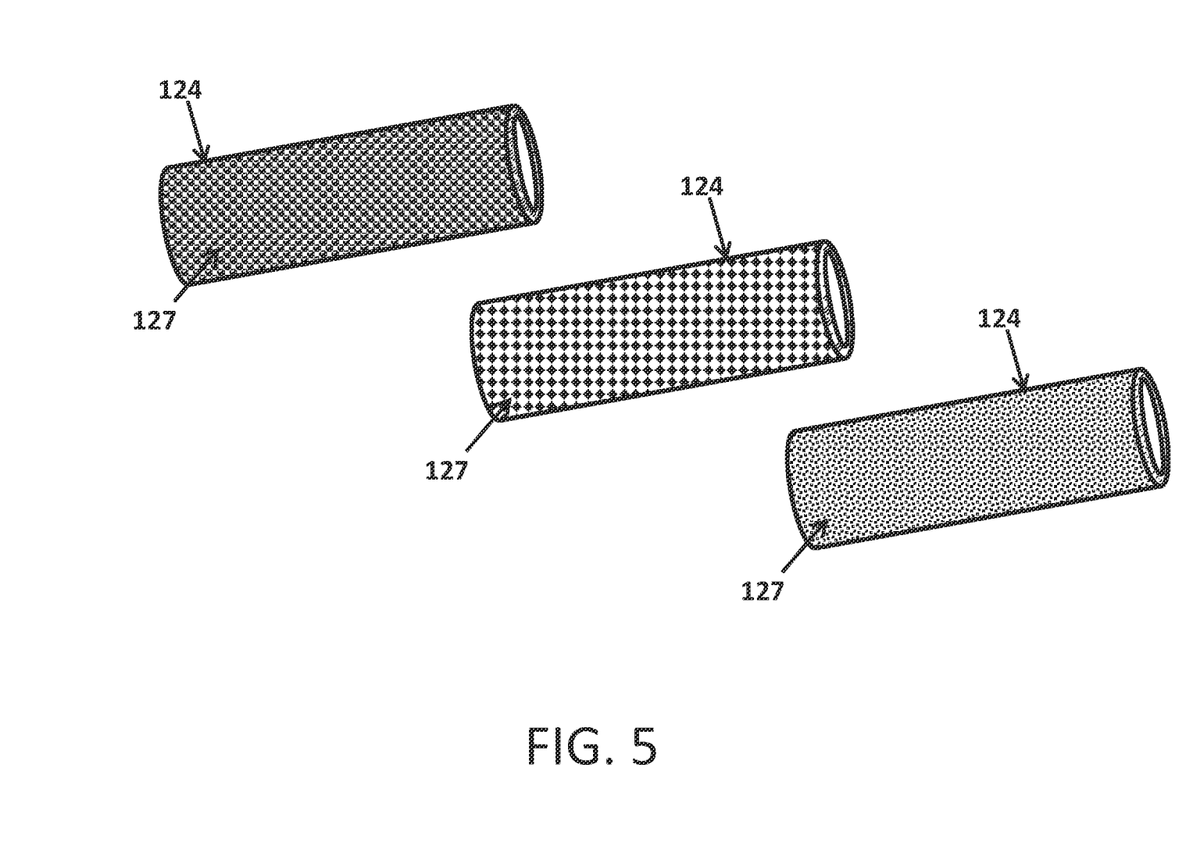
FIG. 5 shows three different patterns upon the outer sleeve of the scalp roller according to the preferred embodiment of the present invention of FIG. 1.

In one embodiment, the scalp roller for tattooing is formed within a kit, wherein there are plurality of outer sleeves 124, as shown in FIG. 5, that are adapted to be placed one at a time around and be removably attached to, usually by friction, an outer surface of the hollow cylindrical body 122, and wherein each of the plurality of outer sleeves 124 is adapted to soak up the liquids, ink in the preferred embodiment, passing through the plurality of spaced apertures 123 and become saturated with the ink. Each of the plurality of outer sleeves 124 are respectively formed to include a pattern 127 different from one another formed on the respective outer surfaces thereof to offer a choice of patterns, and wherein one of the plurality of outer sleeves 124 is chosen to be removably placed around the outer surface of the hollow cylindrical body and is adapted to be saturated with the ink, and used to roll the ink upon a scalp 500 of the person via the roller member 100 and form the chosen pattern 129 on the person's scalp.

Figure 6:
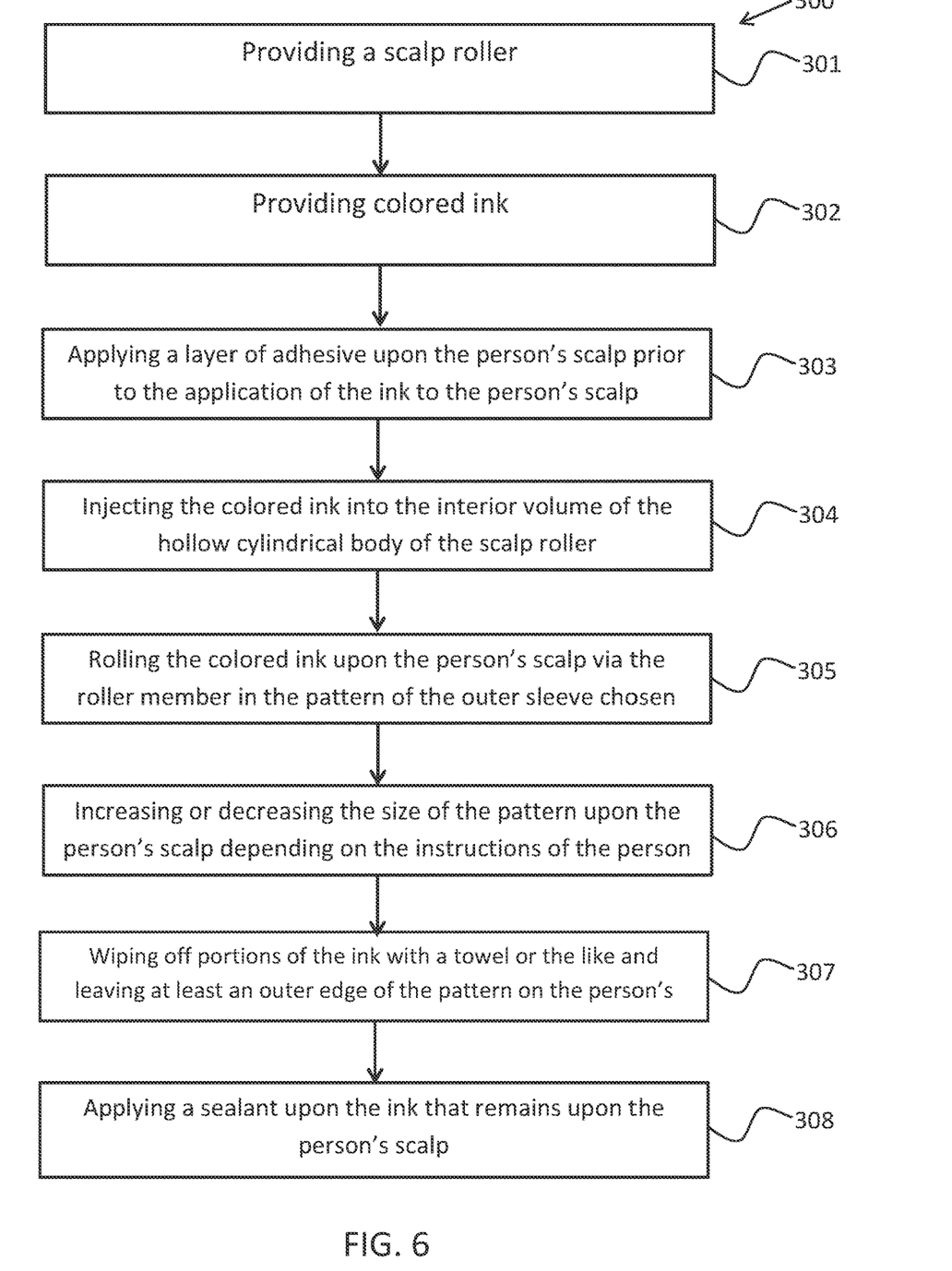
FIG. 6 shows the method steps for tattooing using the scalp roller according to the preferred embodiment of the present invention of FIG. 1.

As shown in FIG. 6, the method 300 of use of the instant scalp roller 100 to prepare for tattooing includes the steps of 301 providing a scalp roller 100 for tattooing as set forth previously; 302 providing colored ink; 304 injecting the colored ink into the interior volume of the hollow cylindrical body; 305 rolling the colored ink upon the person's scalp via the roller member in the pattern of the outer sleeve chosen; 306 and increasing or decreasing the size of the pattern upon the person's scalp depending on the instructions of the person, usually using a towel 600. Further step 305 may include applying a layer of adhesive upon the person's scalp prior to the application of the ink to the person's scalp, in order to increase the friction between the outer sleeve and the person's scalp to thereby avoid sliding between the outer sleeve and the person's scalp. Further step 307 may include wiping off portions of the ink with a towel 600 or the like and leaving at least an outer edge of the pattern on the person's scalp. And, further step 308 may include applying a sealant upon the ink that remains upon the person's scalp in order to allow the ink to remain on the person's scalp for a longer period of time and prior to applying a tattoo upon the person's scalp.

It should be noted that the ink patterns applied to the person's scalp of the instant invention are above/upon the layer of skin of the person's scalp, and the process of tattooing places ink under/below the sub-cutaneous layer of the person's scalp. As such, the ink used in the instant invention can be easily removed while the ink used in tattooing processes are very difficult to remove.

Although specific embodiments have been illustrated and described herein, it will be appreciated by those of ordinary skill in the art that any arrangement, which is calculated to achieve the same purpose, may be substituted for the specific embodiment shown. This application is intended to cover any adaptations or variations of the present invention.

Although the invention has been explained in relation to its preferred embodiment, it is to be understood that many other possible modifications and variations can be made without departing from the spirit and scope of the invention.

What is claimed is:

1. A kit for tattooing comprising:
   a scalp roller comprising:
      a handle including;
         a grip portion;
            wherein said grip portion is adapted to be manipulated by a user's hand; and
         at least one roller attachment member;
            wherein said at least one roller attachment member is connected to said grip portion and is adapted to rotatably hold a roller member thereto;
      said roller member including:
         a hollow cylindrical body including;
            a plurality of spaced apertures;
            wherein said hollow cylindrical body defines an interior volume adapted to hold liquids therein; and
            wherein said hollow cylindrical body is adapted to allow said liquids to pass through said plurality of spaced apertures; and
      a plurality of outer sleeves;
         wherein each of said plurality of outer sleeves are adapted to be placed around and be removably attached to an outer surface of said hollow cylindrical body;
         wherein each of said plurality of outer sleeves are adapted to soak up said liquids passing through said plurality of spaced apertures and become saturated with said liquids; and
         wherein each of said plurality of outer sleeves are respectively formed to include a pattern different from one another formed on respective outer surfaces thereof, and wherein each of said patterns progressively increases the distance between said appearance of said hair follicles; and
         wherein said hollow cylindrical body and said plurality of outer sleeves are flexible, such that said hollow cylindrical body and said plurality of outer sleeves are adapted to flex and conform to the curvature of said person's scalp;
      wherein one of said plurality of outer sleeves is chosen to be removably placed around said outer surface of said hollow cylindrical body, is adapted to be saturated with said liquids, and used to roll said liquids upon a scalp of a person via said roller member and form said pattern on said person's scalp in order to create a pattern on said person's head similar to spaced hair follicles on a person's scalp.

2. The kit for tattooing of claim 1, wherein there are two spaced roller attachment members adapted to rotatably hold said roller member therebetween.

3. The kit for tattooing of claim 1, further comprising colored ink located within said interior volume of said hollow cylindrical body and adapted to be rolled upon said person's scalp via said roller member in said pattern of said chosen outer sleeve.

4. The kit for tattooing of claim 1, wherein said roller member further includes a nipple adapted to allow liquids to be injected into said interior volume.

5. A method of preparing for tattooing including the steps of:
   providing a scalp roller for tattooing comprising:
      a handle including;
         a grip portion;
            wherein said grip portion is adapted to be manipulated by a user's hand; and
         at least one roller attachment member;
            wherein said at least one roller attachment member is connected to said grip portion and is adapted to rotatably hold a roller member thereto;
      said roller member including:
         a hollow cylindrical body including;
            a plurality of spaced apertures;
            wherein said hollow cylindrical body defines an interior volume adapted to hold liquids therein; and
            wherein said hollow cylindrical body is adapted to allow said liquids to pass through said plurality of spaced apertures; and
         an outer sleeve;
            wherein said outer sleeve is adapted to be placed around and be removably attached to an outer surface of said hollow cylindrical body;

wherein said outer sleeve is adapted to soak up said liquids passing through said plurality of spaced apertures and become saturated with said liquids;

wherein said outer sleeve is formed to include a pattern formed on an outer surface thereof, such that when said outer sleeve is saturated with said liquids, said liquids can be rolled upon a scalp of a person via said roller member and form said pattern on said person's scalp in order to create a pattern on said person's head similar to spaced hair follicles on said person's scalp; and wherein said hollow cylindrical body and said outer sleeve are flexible, such that said hollow cylindrical body and said outer sleeve are adapted to flex and conform to the curvature of said person's scalp;

providing colored ink; and injecting said colored ink into said interior volume of said hollow cylindrical body;

rolling said colored ink upon said person's scalp via said roller member in said pattern of said outer sleeve.

6. The method of tattooing of claim 5, further including the steps of:

wiping off portions of said ink and leaving at least an outer edge of said pattern.

7. The method of tattooing of claim 6, further including the steps of:

applying a sealant upon said ink that remains upon said person's scalp.

8. The method of tattooing of claim 5, further including the steps of:

prior to rolling said colored ink upon said person's scalp, applying a layer of adhesive upon said person's scalp to increase the friction between said outer sleeve and said person's scalp to thereby avoid sliding between said outer sleeve and said person's scalp.

9. The method of tattooing of claim 5, wherein there are two spaced roller attachment members adapted to rotatably hold said roller member therebetween.

10. The method of tattooing of claim 5, wherein said roller member further includes a nipple adapted to allow liquids to be injected into said interior volume.

\* \* \* \* \*